US010959679B2

(12) United States Patent
Tseng et al.

(10) Patent No.: US 10,959,679 B2
(45) Date of Patent: Mar. 30, 2021

(54) NONCONTACT SELF-INJECTION-LOCKED SENSOR

(71) Applicants: Sil Radar Technology Inc., Kaohsiung (TW); National Taiwan University of Science and Technology, Taipei (TW)

(72) Inventors: Chao-Hsiung Tseng, New Taipei (TW); Li-Te Yu, Yilan County (TW); Jyun-Kai Huang, Changhua County (TW); Chih-Lin Chang, New Taipei (TW)

(73) Assignees: Sil Radar Technology Inc., Kaohsiung (TW); National Taiwan University of Science and Technology, Taipei (TW)

( * ) Notice: Subject to any disclaimer, the term of this patent is extended or adjusted under 35 U.S.C. 154(b) by 220 days.

(21) Appl. No.: 16/200,826

(22) Filed: Nov. 27, 2018

(65) Prior Publication Data

US 2019/0175117 A1 Jun. 13, 2019

(30) Foreign Application Priority Data

Dec. 12, 2017 (TW) .................................. 106143627

(51) Int. Cl.
*A61B 5/00* (2006.01)
*H01Q 5/328* (2015.01)
(Continued)

(52) U.S. Cl.
CPC .............. *A61B 5/7228* (2013.01); *A61B 5/05* (2013.01); *H01Q 3/28* (2013.01); *H01Q 5/328* (2015.01);
(Continued)

(58) Field of Classification Search
CPC ....... A61B 5/0507; A61B 5/0205; A61B 5/05; A61B 5/7228; A61B 5/024; A61B 5/0803;
(Continued)

(56) References Cited

U.S. PATENT DOCUMENTS 8,721,554 B2  5/2014 Lin et al.
9,603,555 B2 * 3/2017 Horng ................. A61B 5/0816
(Continued)

FOREIGN PATENT DOCUMENTS

CN      104703533 A    6/2015
TW      201315437      4/2013
(Continued)

OTHER PUBLICATIONS

Fu-Kang Wang, Tzyy-Sheng Horng, Kang-Chun Peng, Je-Kaun Jau, J. Yu Li, Single-Antenna Doppler Radars Using Self and Mutual Injection Locking for Vital Sign Detection With Random Body Movement Cancellation, Dec. 2011, IEEE Transactions on Microwave Theory and Techniques, vol. 59, No. 12, 3577-3587 (Year: 2011).*

(Continued)

*Primary Examiner* — Olumide Ajibade Akonai
(74) *Attorney, Agent, or Firm* — Demian K. Jackson; Jackson IPG PLLC

(57) ABSTRACT

In a noncontact self-injection-locked sensor, a self-injection-locked oscillating integrated antenna is designed to radiate a signal to a subject and be injection-locked by a reflect signal reflected from the subject. Owing to the reflect signal is phase-modulated by vital signs of the subject, a demodulator is provided to demodulate an injection-locked signal of the self-injection-locked oscillating integrated antenna to obtain a vital signal of the subject.

16 Claims, 7 Drawing Sheets

(51) Int. Cl.
*H01Q 3/28* (2006.01)
*A61B 5/05* (2021.01)
*H01Q 9/04* (2006.01)
*A61B 5/08* (2006.01)
*A61B 5/024* (2006.01)
*A61B 5/113* (2006.01)
*G01S 13/34* (2006.01)
*G01S 7/41* (2006.01)
*G01S 13/88* (2006.01)
*G01S 13/32* (2006.01)

(52) U.S. Cl.
CPC ........ H01Q 9/0442 (2013.01); *A61B 5/02444* (2013.01); *A61B 5/0816* (2013.01); *A61B 5/113* (2013.01); *G01S 7/415* (2013.01); *G01S 13/32* (2013.01); *G01S 13/34* (2013.01); *G01S 13/88* (2013.01)

(58) Field of Classification Search
CPC ........ A61B 2562/0228; A61B 2562/04; A61B 5/0816; A61B 5/02444; A61B 5/113; A61B 5/681; G01S 13/583; G01S 13/88; G01S 13/003; G01S 13/536; G01S 7/415; G01S 7/354; G01S 13/32; G01S 13/34; G01S 1/02; G01S 7/03; H01Q 5/328; H01Q 3/28; H01Q 9/0442; H03L 7/24
See application file for complete search history.

(56) References Cited

U.S. PATENT DOCUMENTS

| | | | | |
|---|---|---|---|---|
| 2010/0198083 | A1* | 8/2010 | Lin | G06F 17/14 600/484 |
| 2012/0209087 | A1* | 8/2012 | Horng | G01S 7/354 600/301 |
| 2012/0245479 | A1* | 9/2012 | Ganesh | A61B 5/7264 600/508 |
| 2014/0024917 | A1* | 1/2014 | McMahon | G01S 7/282 600/407 |
| 2014/0128748 | A1* | 5/2014 | Horng | G01S 13/88 600/484 |
| 2015/0241555 | A1* | 8/2015 | Lin | A61B 5/0816 702/56 |
| 2018/0081030 | A1* | 3/2018 | McMahon | G01S 13/524 |
| 2018/0235481 | A1* | 8/2018 | Liu | A61B 5/1135 |
| 2018/0263502 | A1* | 9/2018 | Lin | A61B 5/7207 |

FOREIGN PATENT DOCUMENTS

| | | |
|---|---|---|
| TW | 2013351353 | 12/2013 |
| TW | 201428325 | 7/2014 |
| TW | I514193 | 12/2015 |
| TW | I556797 | 11/2016 |

OTHER PUBLICATIONS

Fu-Kang Wang, Mu-Cyun Tang, Sheng-Chao Su, Tzyy-Sheng Horng, Wrist Pulse Rate Monitor Using Self-Injection-Locked Radar Technology, Oct. 26, 2016, Biosensors, 2016, 6, 54, pp. 1-12 (Year: 2016).*
F. Wang, T. Horng, K. Peng, J. Jau, J. Li, C. Cheng, Detection of Concealed Individuals Based on Their Vital Signs by Using a See-Through-Wall Imaging System With a Self-Injection-Locked Radar, Jan. 2013, IEEE Transactions on Microwave Techniques and applications, vol. 61, No. 1, pp. 696-704 (Year: 2013).*
Fu-Kang Wang, You-Rung Chou, Yen-Chen Chiu, Mu-Cyun Tang, Tzyy-Sheng Horng, Chest-Worn Health Monitor Based on a Bistatic Self-Injected-Locked Radar, 2015, IEEE transactions on Biomedical Engineering, vol. 62, pp. 2931-2940 (Year: 2015).*
F. Wang, C. Li, C. Hsiao, T. Horng, J. Lin, K. Peng, J. Jau, J. Li, C. Chen, A Novel Vital-Sign Sensor Based on a Self-Injection-Locked Oscillator, Dec. 2010, IEEE Transactions on Microwave Theory and Techniques, vol. 58, No. 12, pp. 4112-4120 (Year: 2010).*
Taiwanese Notice of Allowance dated Oct. 3, 2018 for Taiwanese Patent Application No. 106143627, 3 pages.
Chao-Hsiung Tseng et al., A Cost-Effective Wearable Vital-Sign Sensor with Self-Oscillating Active Antenna Based on Envelope Detection Technique, 2017 IEEE MTT-S International Microwave Symposium (IMS), Jun. 4-9, 2017.
Chao-Hsiung Tseng et al., A Wearable Self-Injection-Locked Sensor With Active Integrated Antenna and Differentiator-Based Envelope Detector for Vital-Sign Detection From Chest Wall and Wrist, IEEE Transactions on Microwave Theory and Techniques, vol. 66, No. 5, May 2018, Jan. 4, 2018.
Chao-Hsiung Tseng et al., Self-Injection-Locked Radar Sensor with Active-Integrated-Antenna and Differentiator-Based Demodulator for Noncontact Vital Sign Detection, 2018 IEEE Topical Conference on Wireless Sensors and Sensor Networks (WiSNet), Jan. 14-17, 2018.

* cited by examiner

NONCONTACT SELF-INJECTION-LOCKED SENSOR

FIELD OF THE INVENTION

This invention generally relates to a sensor, and more particularly to a noncontact self-injection-locked (SIL) sensor.

BACKGROUND OF THE INVENTION

Wearable healthcare devices are the potential consumer electronics and usually use photoelectric sensor to detect vital signs. In conventional photoelectric sensor, a light is applied to human skin and capturing the images of the skin by a camera. The skin images are used to observe light intensity variation which is caused by the volume variation of blood flowing through the human skin. As a result, the photoelectric sensor can measure the heartbeat rate according the light intensity variation. However, the photoelectric sensor has to be placed on the human skin tightly for accurate detection because it is sensitive to ambient light. That is the reason why the healthcare device is usually designed as a wristwatch. Additionally, the user wearing the healthcare device for a long time may feel uncomfortable due to the healthcare device is attached to the skin tightly.

SUMMARY

In the present invention, a SIL oscillating integrated antenna is provided to radiate an oscillation signal to a subject and receive a reflect signal from the subject. The reflect signal brings SIL oscillating integrated antenna to a SIL state. Besides, the reflect signal is modulated by vital signs of the subject (e.g. respiration, heartbeat and wrist pulse), so demodulating the output signal of the SIL oscillating integrated antenna can acquire a vital signal of the subject, that is a contactless way to acquire the vital signal. Moreover, the SIL oscillating integrated antenna plays both roles of signal radiating/receiving element and oscillating element such that the output signal contains both the components of amplitude modulation and frequency modulation, and the SIL oscillating integrated antenna exhibits highly sensitivity for sensing tiny vibration.

A noncontact SIL sensor of the present invention includes a SIL oscillating integrated antenna and a demodulator. The SIL oscillating integrated antenna includes an antenna and an active element which are electrically connected to each other. The antenna is configured for oscillation with the active element to generate an oscillation signal and configured for frequency selection. And the antenna is further configured to radiate the oscillation signal to a subject and receive a reflect signal reflected from the subject to bring the self-injection-locked oscillating integrated antenna to a SIL state. The oscillation signal is modulated by the vital signs of the subject to become a frequency- and amplitude-modulated signal. The demodulator includes a differentiator and an envelope detector. The differentiator is electrically connected to the self-injection-locked oscillating integrated antenna and configured to receive and differentiate the frequency- and amplitude-modulated signal into an amplitude-modulated signal. The envelope detector is electrically connected to the differentiator and is configured to demodulate the amplitude-modulated signal in amplitude to obtain a vital signal of the subject.

In the present invention, owing to the SIL oscillating integrated antenna has capabilities of oscillating, radiating and receiving signals, it can acquire the both amplitude and frequency modulation components of signals caused by vital signs under the SIL state and precisely detect vital signs of the subject after demodulation. Moreover, the demodulator can realizes the signal demodulation in a simple architecture so the noncontact SIL sensor is capable of operating under extremely high frequency conditions and sensing pretty small vibration well. The noncontact SIL sensor of the present invention is available for further potential applications.

DETAILED DESCRIPTION OF THE INVENTION

Figure 1:
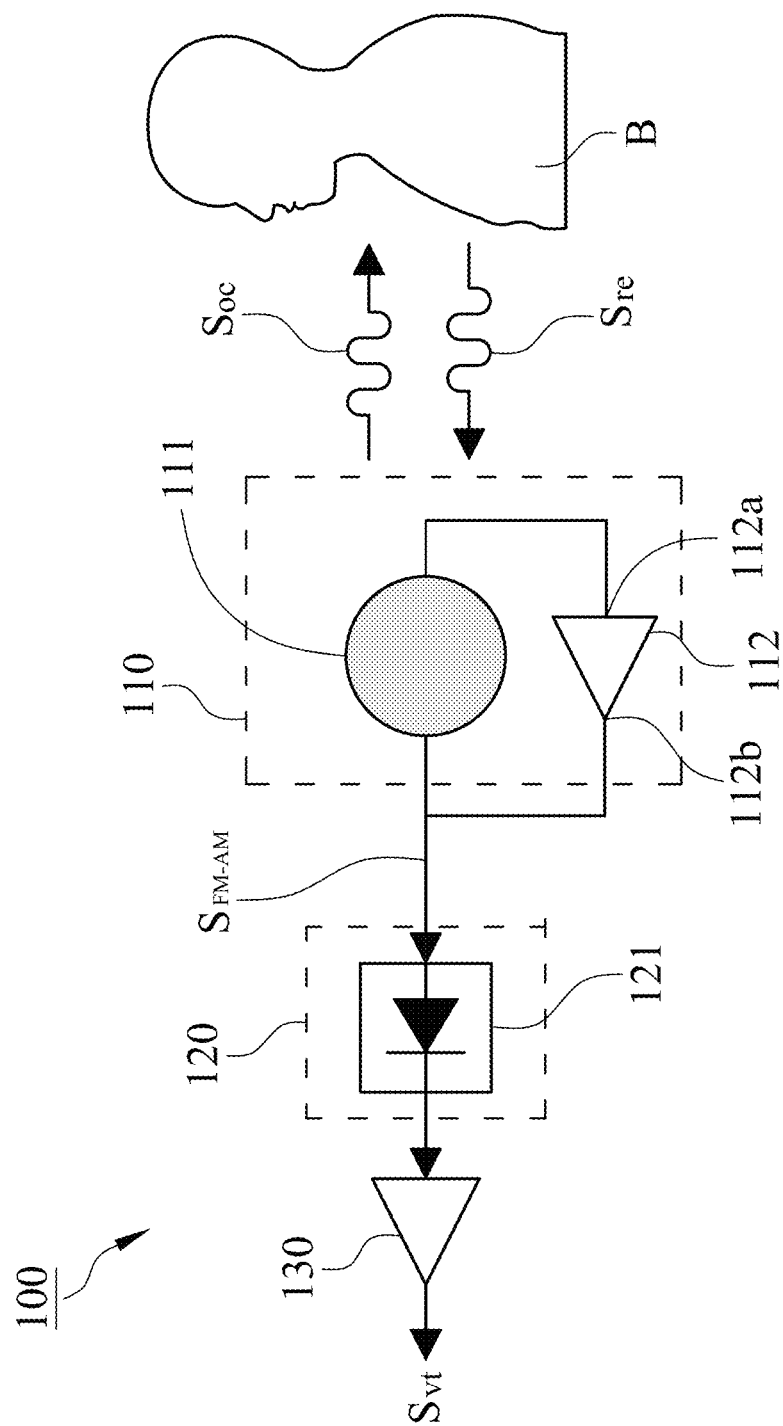
FIG. 1 is a circuit diagram illustrating a noncontact SIL sensor in accordance with a first embodiment of the present invention.

A noncontact SIL sensor 100 of a first embodiment of the present invention is shown in FIG. 1. The noncontact SIL sensor 100 includes a SIL oscillating integrated antenna 110, a demodulator 120 and a baseband amplifier 130.

The SIL oscillating integrated antenna 110 includes an antenna 111 and an active element 112 electrically connected to the antenna 111. In the first embodiment, the antenna 111 is a plane printed antenna and the active element 112 is a solid-state amplifier. Furthermore, the active element 112 of the first embodiment has an input port 112a and an output port 112b which are both electrically connected to the antenna 111 to form a loop configuration.

In the first embodiment, the antenna 111 is configured for oscillation with the active element 112 to generate an oscillation signal $S_{oc}$ and for frequency-selection. Furthermore, the antenna 111 is also employed to radiate the oscillation signal $S_{oc}$ to a subject B. After the oscillation signal $S_{oc}$ contacts the subject B, a reflect signal $S_{re}$ is reflected from the subject B and received by the antenna 111. The reflect signal $S_{re}$ injects into and locks the SIL oscillating integrated antenna 110 in a SIL state. The SIL oscillating integrated antenna 110 is not only used as a signal radiating/receiving element but also involved in oscillation. As a result, the oscillation signal $S_{oc}$ is modulated by a vital sign of the subject B (e.g. respiration, heartbeat and wrist pulse) in frequency and amplitude to become a frequency- and amplitude-modulated signal $S_{FM-AM}$.

With reference to FIG. 1, the demodulator 120 is electrically connected to the SIL oscillating integrated antenna 110 in order to receive the frequency- and amplitude-modulated signal $S_{FM-AM}$. The demodulator 120 is configured to demodulate the frequency- and amplitude-modulated signal $S_{FM-AM}$ to obtain a vital signal $S_{vt}$ of the subject B. In the first embodiment, the demodulator 120 is an envelope detector 121 configured to proceed amplitude demodulation of the frequency- and amplitude-modulated signal $S_{FM-AM}$. The envelope detector 121 can extract the amplitude modulation components of the frequency- and amplitude-modulated signal $S_{FM-AM}$ to obtain the vital signal $S_{vt}$. The baseband amplifier 130 is electrically connected to the demodulator 120 to receive and amplify the vital signal $S_{vt}$.

Because the noncontact SIL sensor 100 of the first embodiment can acquire the vital sign $S_{vt}$ of the subject B through the amplitude demodulation proceeded by the envelope detector 121 only, the demodulator 120, compared with other radars, has advantages of simple architecture and low costs. Moreover, the operation frequency band of the SIL oscillating integrated antenna 110 can be increased to millimeter wave range (30-300 GHz) to improve sensitivity of sensing tiny vibration dramatically so that the noncontact SIL sensor 100 can be applied to further potential applications, not only applied to detect vital signs of large subjects with large vibration movement.

Figure 2:
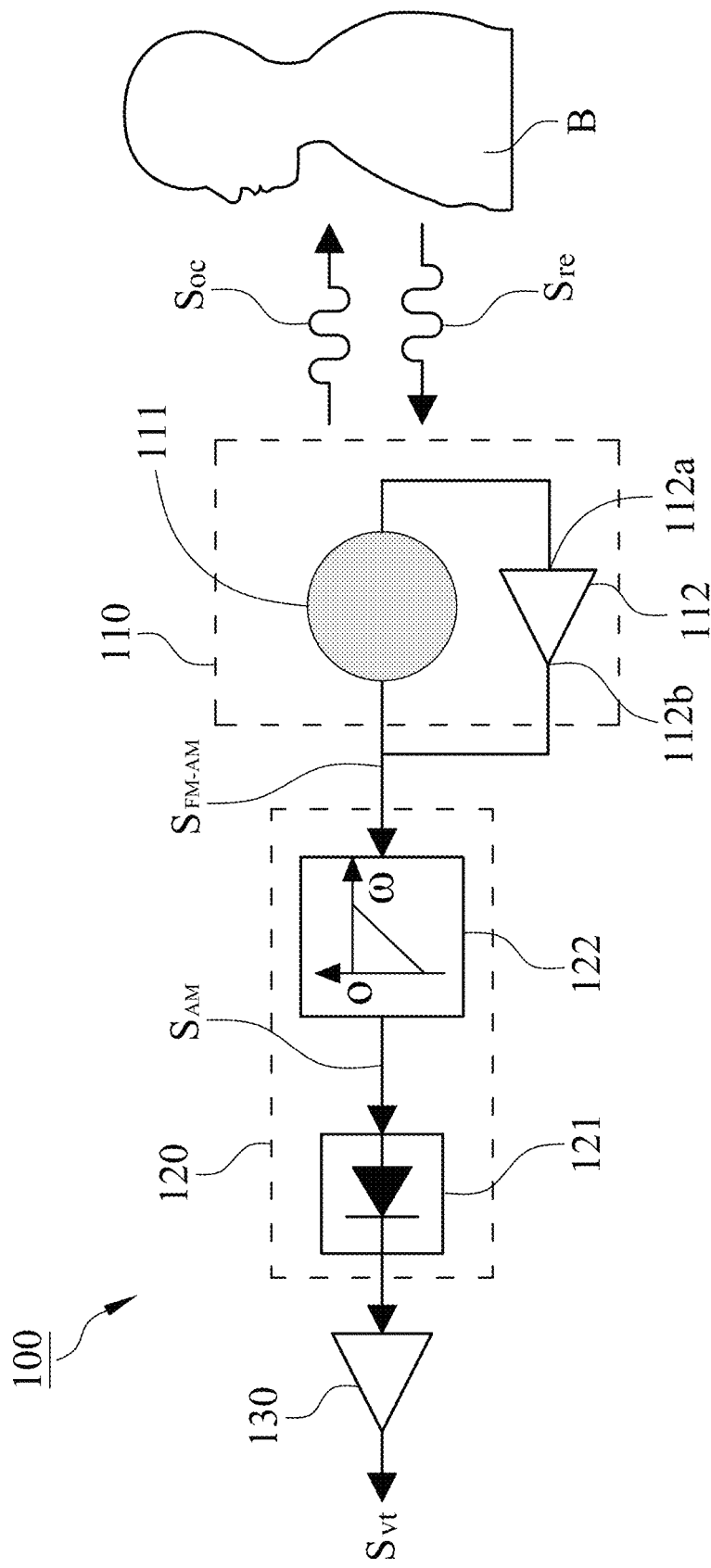
FIG. 2 is a circuit diagram illustrating a noncontact SIL sensor in accordance with a second embodiment of the present invention.

With reference to FIG. 2, different to the first embodiment, the demodulator 120 in a second embodiment further includes a differentiator 122 which is added between and electrically connected to the SIL oscillating integrated antenna 110 and the envelope detector 121. The differentiator 122 is configured to receive the frequency- and amplitude-modulated signal $S_{FM-AM}$ from the SIL oscillating integrated antenna 110 and differentiate the frequency- and amplitude-modulated signal $S_{FM-AM}$ to convert the frequency modulation components into the amplitude modulation components. Consequently, the frequency- and amplitude-modulated signal $S_{FM-AM}$ is converted to an amplitude-modulated signal $S_{AM}$ to improve the sensitivity of sensing vital signs of the subject B. The envelope detector 121, electrically connected to the differentiator 122, is configured to receive and amplitude-demodulate the amplitude-modulated signal $S_{AM}$ for obtaining the vital signal $S_{vt}$. Because the noncontact SIL sensor 100 of the second embodiment further utilize the differentiator 122 to convert frequency modulation to amplitude modulation, frequency and amplitude modulations of the oscillation signal $S_{oc}$ caused by vital signs of the subject B are fused to further enhance the sensitivity of the noncontact SIL sensor 100 for sensing tiny vibrations.

In the second embodiment, the differentiator 122 is a microstrip differentiator, and the operation frequency of the differentiator 122 is substantially the same as the frequency of the frequency- and amplitude-modulated signal $S_{FM-AM}$. Particularly, the noncontact SIL sensor 100 of the second embodiment has better sensitivity when the frequency of the frequency- and amplitude-modulated signal $S_{FM-AM}$ and the operation frequency of the differentiator 122 are higher than or equal to 300 MHz.

Figure 3:
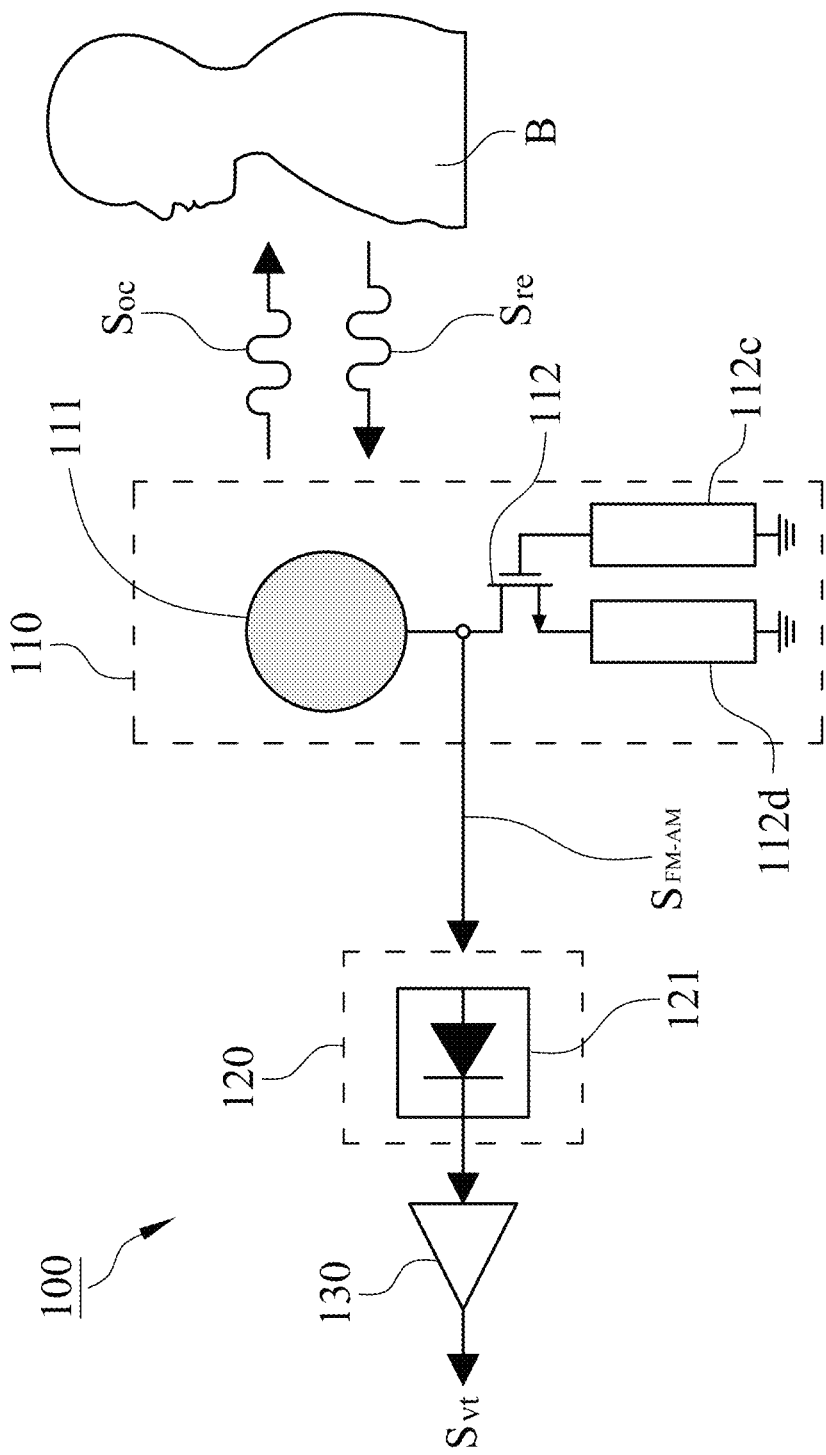
FIG. 3 is a circuit diagram illustrating a noncontact SIL sensor in accordance with a third embodiment of the present invention.
Figure 4:
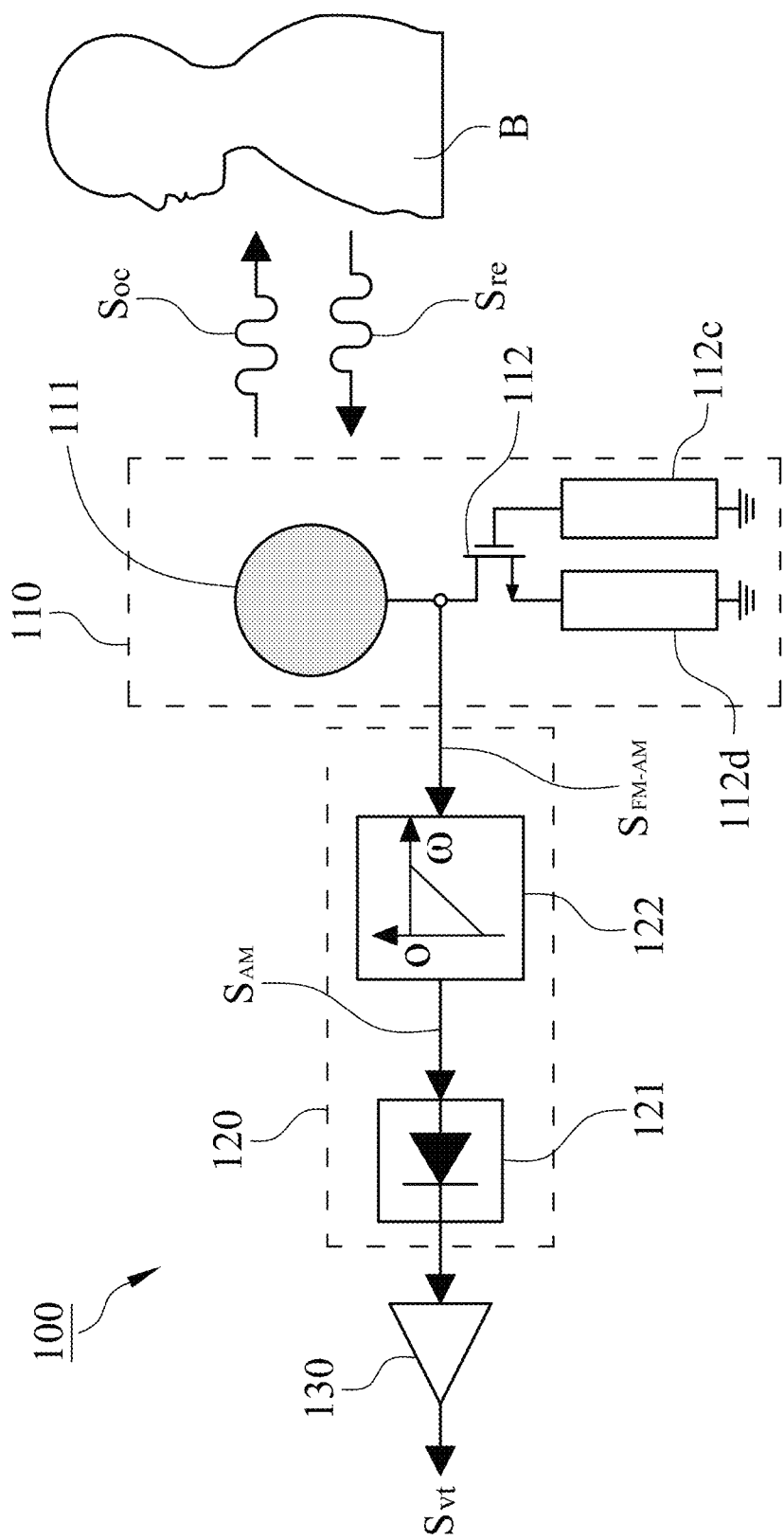
FIG. 4 is a circuit diagram illustrating a noncontact SIL sensor in accordance with a fourth embodiment of the present invention.

FIGS. 3 and 4 represent third and fourth embodiments of the present invention. The active element 112 in the third and fourth embodiments is a solid-state transistor having a gate, a source and a drain, different to the solid-state amplifier in the first and second embodiments. The drain of the active element 112 is coupled to the antenna 111, the gate of the active element 112 is connected to ground via a first reactance element 112c, and the source of the active element 112 is connected to ground via a second reactance element 112d such that the antenna 111 and the active element 112 constitute a reflect type configuration. The first reactance element 112c and the second reactance element 112d may be transmission lines capable of be operated under high frequency conditions. Identical to the first and second embodiments, the antenna 111 and the active element 112 in the third and fourth embodiments are employed for oscillation and the oscillation signal $S_{oc}$ generation. The antenna 111 is configured to radiate the oscillation signal $S_{oc}$ to the subject B and receive the reflect signal $S_{re}$ reflected from the subject B. The reflect signal $S_{re}$ brings the SIL oscillating integrated antenna 110 into the SIL state to output the frequency- and amplitude-modulated signal $S_{FM-AM}$. The demodulator 120 is configured to demodulate the frequency- and amplitude-modulated signal $S_{FM-AM}$ to acquire the vital signal $S_{vt}$.

With reference to FIGS. 3 and 4, in the reflect type configuration, the demodulator 120 of the third embodiment only uses the envelope detector 121 to perform the amplitude demodulate process of the frequency- and amplitude-modulated signal $S_{FM-AM}$ to obtain the vital signal $S_{vt}$, and the demodulator 120 of the fourth embodiment uses the differentiator 122 to convert the frequency modulation components to the amplitude modulation components and then uses the envelope detector 121 to amplitude-demodulate the amplitude-modulated signal $S_{AM}$ to obtain the vital signal $S_{vt}$.

Figure 5:
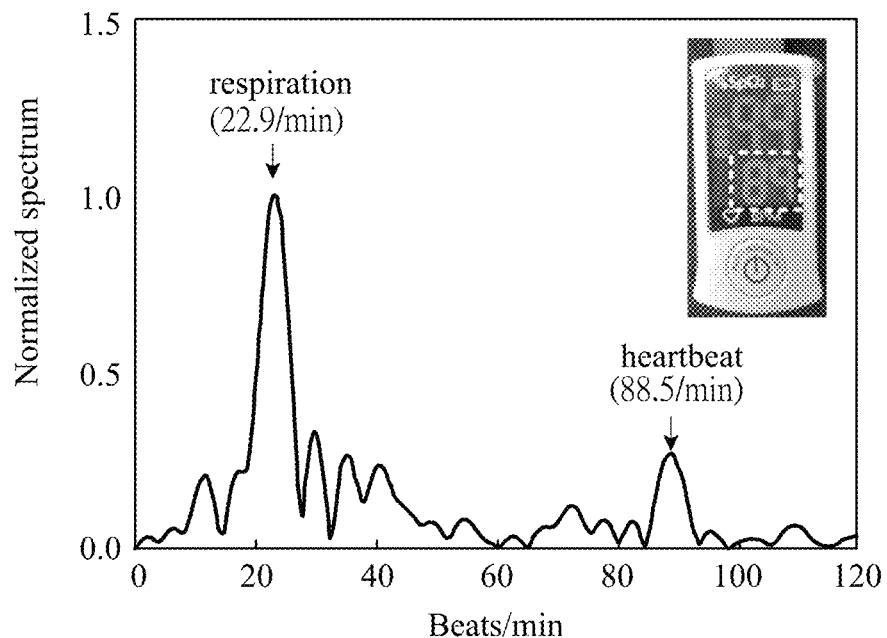
FIG. 5 is a vital-sign waveform diagram of human chest detected by the noncontact SIL sensor in accordance with the second embodiment of the present invention.
Figure 6:
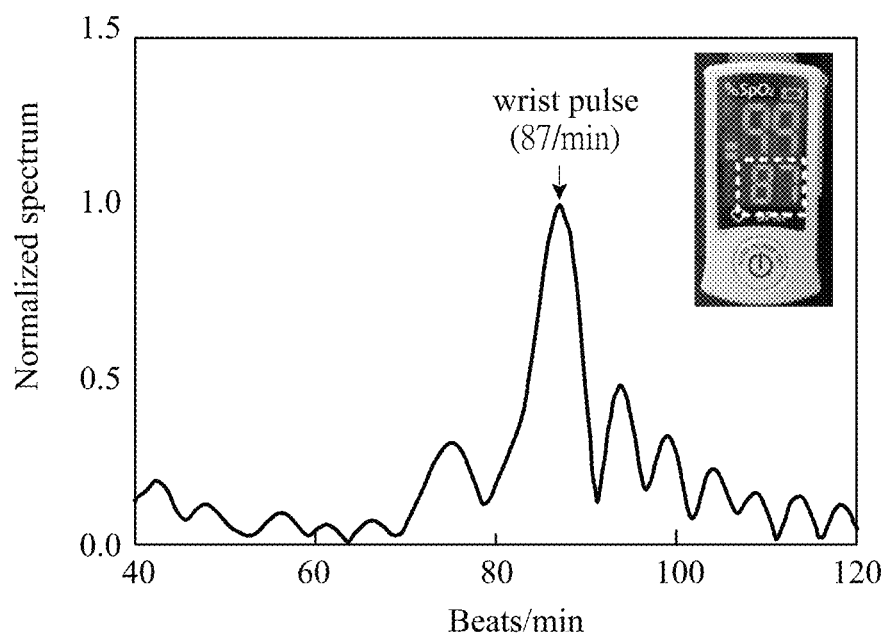
FIG. 6 is a vital-sign waveform diagram of human wrist detected by the noncontact SIL sensor in accordance with the second embodiment of the present invention.

FIG. 5 is a test result of the vital signal $S_{vt}$ using the noncontact SIL sensor 100 of the second embodiment. The SIL sensor is wore on a human chest with a separated distance due to clothes. Two clear spectrum peaks of the vital signal $S_{vt}$ represent respiration and heartbeat rates, and the measured heartbeat rate agrees the human heartbeat rate (the data shown on upper right corner of FIG. 5) acquired by a finger pulse oximeter well. FIG. 6 is a test result of the vital signal $S_{vt}$ by placing the noncontact SIL sensor 100 of the second embodiment on the human wrist. The spectrum peak of wrist pulse is identified, and there is no spectrum peak representing respiration in the vital signal $S_{vt}$ because the SIL sensor located on the human wrist cannot detect respiration. The measured wrist pulse rate agrees the human heartbeat rate (the data shown on upper right corner of FIG. 6) detected by the finger pulse oximeter well. The test results demonstrate the noncontact SIL sensor 100 of the present invention can sense human vital signs precisely by way of contactless.

Figure 7:
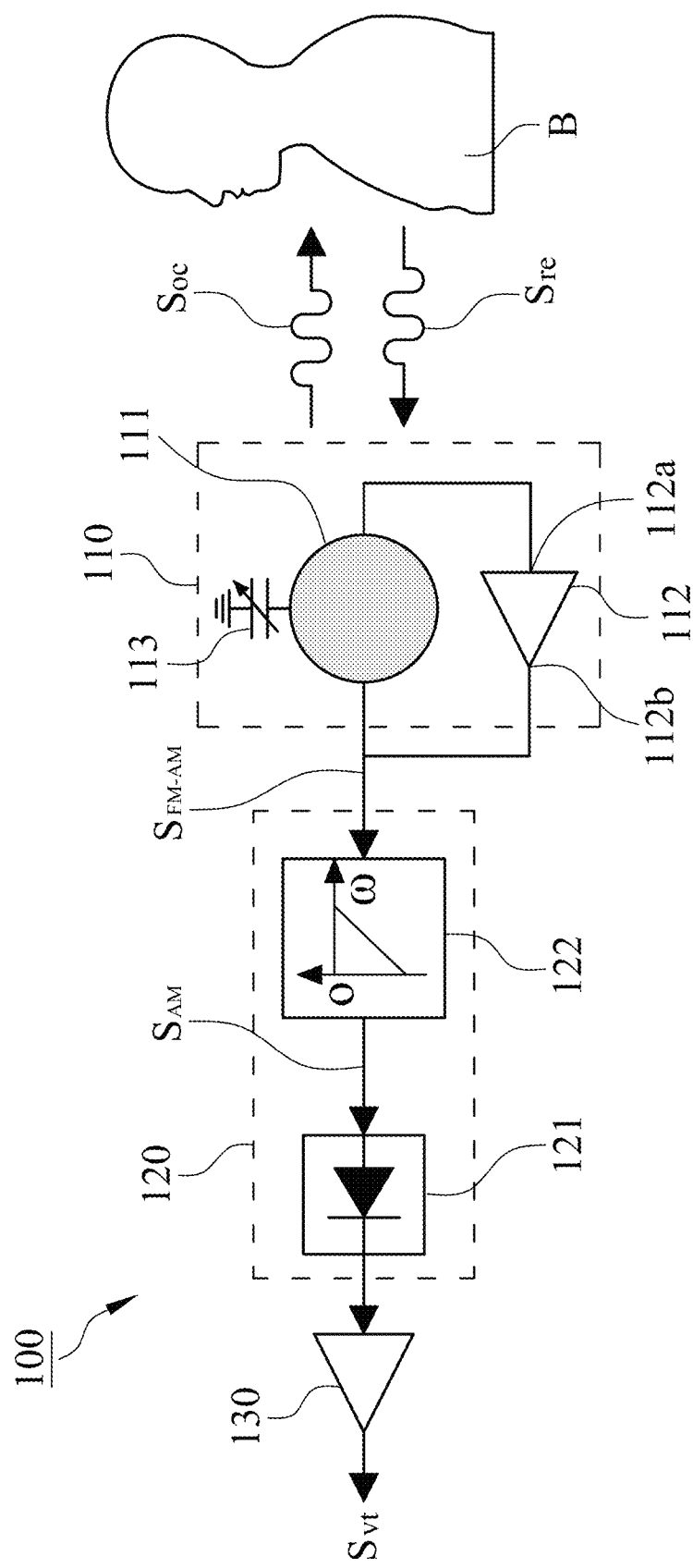
FIG. 7 is a circuit diagram illustrating a noncontact SIL sensor in accordance with a fifth embodiment of the present invention.
Figure 8:
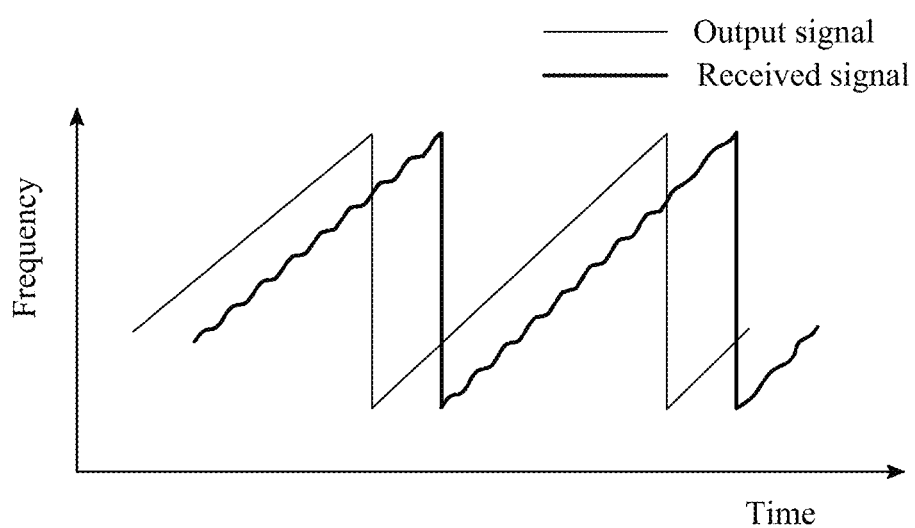
FIG. 8 is a waveform diagram of output signal and received signal when the noncontact SIL sensor in accordance with the fifth embodiment of the present invention produces a linear variation in frequency.

FIG. 7 shows a fifth embodiment of the present invention. The difference to the second embodiment is the SIL oscillating integrated antenna 110 further includes an adjustable capacitance 113. One end of the adjustable capacitance 113 is electrically connected to the antenna 111 and the other end of the adjustable capacitance 113 is connected to ground. The capacitance value of the adjustable capacitance 113 can influence the frequency selection of the antenna 111 to adjust the frequency of the SIL oscillating integrated antenna 110. With reference to FIG. 8, when the SIL oscillating integrated antenna 110 produces a linear variation in frequency because of the adjustable capacitance 113, the SIL oscillating integrated antenna 110 is configured as a frequency-modulated continuous-wave radar (FMCW) which can demodulate the received signals by the demodulator 120 and perform a fast-Fourier transform (FFT) to calculate the distance between the SIL oscillating integrated antenna 110 and the subject B.

In the present invention, the SIL oscillating integrated antenna 110 is provided for oscillating, radiating and receiving signals such that it can acquire the amplitude and frequency modulation components in signals caused by vital signs of the subject B in the SIL state and demodulate the signals to detect the vital signs of the subject B precisely. Furthermore, owing to the architecture of the demodulator 120 used for demodulation is simple, the noncontact SIL sensor 100 can operate in extremely high frequency conditions and is highly sensitive to tiny vibration. For these reasons, the noncontact SIL sensor 100 of the present invention can be applied to further potential applications.

While this invention has been particularly illustrated and described in detail with respect to the preferred embodiments thereof it will be clearly understood by those skilled in the art that is not limited to the specific features shown and described and various modified and changed in form and details may be made without departing from the spirit and scope of this invention.

What is claimed is:

1. A noncontact self-injection-locked sensor comprising:
   a self-injection-locked oscillating integrated antenna including an antenna and an active element which are electrically connected to each other, the antenna is configured for oscillation with the active element to generate an oscillation signal and configured for frequency selection, and the antenna is further configured to radiate the oscillation signal to a subject and receive a reflect signal reflected from the subject to bring the self-injection-locked oscillating integrated antenna to a self-injection-locked state, wherein the oscillation signal is modulated by the vital sign of the subject to become a frequency- and amplitude-modulated signal; and
   a demodulator including a differentiator and an envelope detector, the differentiator is electrically connected to the self-injection-locked oscillating integrated antenna and configured to receive and differentiate the frequency- and amplitude-modulated signal into an amplitude-modulated signal, the envelope detector is electrically connected to the differentiator and is configured to demodulate the amplitude-modulated signal in amplitude to obtain a vital signal of the subject.

2. The noncontact self-injection-locked sensor in accordance with claim 1, wherein the differentiator is a microstrip differentiator, and an operation frequency of the differentiator is substantially the same as a frequency of the frequency- and amplitude-modulated signal.

3. The noncontact self-injection-locked sensor in accordance with claim 2, wherein the frequency of the frequency- and amplitude-modulated signal and the operation frequency of the differentiator are higher than or equal to 300 MHz.

4. The noncontact self-injection-locked sensor in accordance with claim 1, wherein the antenna is a plane printed antenna.

5. The noncontact self-injection-locked sensor in accordance with claim 4, wherein the self-injection-locked oscillating integrated antenna further includes an adjustable capacitance, one end of the adjustable capacitance is electrically connected to the antenna and the other end of the adjustable capacitance is connected to ground.

6. The noncontact self-injection-locked sensor in accordance with claim 4, wherein the active element is a solid-state amplifier, and the active element has an input port and an output port which are both electrically connected to the antenna.

7. The noncontact self-injection-locked sensor in accordance with claim 4, wherein the active element is a solid-state element, a drain of the active element is coupled to the antenna, a gate of the active element is connected to ground via a first reactance element and a source of the active element is connected to ground via a second reactance element.

8. The noncontact self-injection-locked sensor in accordance with claim 2, wherein the antenna is a plane printed antenna.

9. The noncontact self-injection-locked sensor in accordance with claim 8, wherein the self-injection-locked oscillating integrated antenna further includes an adjustable capacitance, one end of the adjustable capacitance is electrically connected to the antenna and the other end of the adjustable capacitance is connected to ground.

10. The noncontact self-injection-locked sensor in accordance with claim 8, wherein the active element is a solid-state amplifier, and the active element has an input port and an output port which are both electrically connected to the antenna.

11. The noncontact self-injection-locked sensor in accordance with claim 8, wherein the active element is a solid-state element, a drain of the active element is coupled to the antenna, a gate of the active element is connected to ground via a first reactance element and a source of the active element is connected to ground via a second reactance element.

12. The noncontact self-injection-locked sensor in accordance with claim 3, wherein the antenna is a plane printed antenna.

13. The noncontact self-injection-locked sensor in accordance with claim 12, wherein the self-injection-locked oscillating integrated antenna further includes an adjustable capacitance, one end of the adjustable capacitance is electrically connected to the antenna and the other end of the adjustable capacitance is connected to ground.

14. The noncontact self-injection-locked sensor in accordance with claim 12, wherein the active element is a solid-state amplifier, and the active element has an input port and an output port which are both electrically connected to the antenna.

15. The noncontact self-injection-locked sensor in accordance with claim 12, wherein the active element is a solid-state element, a drain of the active element is coupled to the antenna, a gate of the active element is connected to ground via a first reactance element and a source of the active element is connected to ground via a second reactance element.

16. The noncontact self-injection-locked sensor in accordance with claim 1 further comprising a baseband amplifier, wherein the baseband amplifier is electrically connected to the demodulator and configured to receive and amplify the vital signal.

* * * * *